United States Patent [19]

Stempfle et al.

[11] Patent Number: 4,657,486

[45] Date of Patent: Apr. 14, 1987

[54] PORTABLE INFUSION DEVICE

[76] Inventors: Julius E. Stempfle, 12007 SW. 60 Ave., Portland, Oreg. 97219; Roger D. Partipilo, Rte. 5, Box 430, Coosbay, Oreg. 97420

[21] Appl. No.: 745,097

[22] Filed: Jun. 17, 1985

Related U.S. Application Data

[60] Division of Ser. No. 570,327, Jan. 13, 1984, abandoned, Division of Ser. No. 201,113, Oct. 28, 1980, abandoned, which is a continuation of Ser. No. 888,354, Mar. 20, 1978, abandoned, which is a continuation-in-part of Ser. No. 614,421, Sep. 18, 1975, abandoned, which is a continuation-in-part of Ser. No. 421,031, Dec. 3, 1973, abandoned.

[51] Int. Cl.⁴ .................... F04B 49/00; A61M 5/00
[52] U.S. Cl. ................................. 417/12; 604/153
[58] Field of Search .................. 417/12, 474, 477; 604/67, 123, 131, 150, 151, 152, 153

[56] References Cited

U.S. PATENT DOCUMENTS

| 1,874,667 | 8/1932 | Wada | 417/474 |
| 2,925,814 | 2/1960 | Vibber | 604/152 X |
| 3,083,647 | 4/1963 | Muller | 417/474 |
| 3,736,930 | 6/1973 | Georgi | 604/67 |
| 4,013,074 | 3/1977 | Siposs | 604/891 |
| 4,140,117 | 2/1979 | Buckles | 604/132 |
| 4,150,672 | 4/1979 | Whitney | 604/155 |
| 4,498,843 | 2/1985 | Schneider et al. | 604/67 |

Primary Examiner—Leonard E. Smith
Attorney, Agent, or Firm—Jay M. Cantor

[57] ABSTRACT

A portable infusion device for injecting medicinal fluids into a human or animal body by means of a positive pressure pump that is automatically operated at selected time intervals to inject accurate amounts of fluid medicine into the body.

5 Claims, 40 Drawing Figures

PORTABLE INFUSION DEVICE

CROSS REFERENCE TO RELATED APPLICATION

This application is a division of Ser. No. 570,327 filed Jan. 13, 1984, now abandoned, which is a division of Ser. No. 201,113, filed Oct. 28, 1980, now abandoned, which is a continuation of Ser. No. 888,354 filed Mar. 20, 1978 (now abandoned), which is a continuation-in-part of Ser. No. 614,421 filed Sept. 18, 1975 (now abandoned), which is a continuation-in-part of Ser. No. 421,031 filed Dec. 3, 1974 (now abandoned).

BACKGROUND OF THE INVENTION

Certain kinds of patients require periodic injections of fluid medicine into their bodies. An example of one kind of patient is a cancer patient who needs to have injected into his body exact amounts of medicine at periodic periods of time.

One way to accomplish this is to hospitalize the patient for the time necessary to inject the medicine at periodic times by hospital personnel. This ties up needed hospital space and personnel because in many such cases, the patient can be ambulatory, but in order to obtain proper medication, he must be hospitaized. The administering of such medication by hospital personnel can result in inaccurate doses and at inprecise times.

Another way to medicate such a patient is to utilize a known portable infusion device as disclosed in U.S. Pat. No. 3,384,080 which constantly injects therapeutic fluids into a human body by means of a pump that is powered by a spring motor, the speed of which is controlled by a watch escapement unit. This device is not satisfactory because it constantly feeds medicine into the body, the spring motor has to be manually rewound, the pump uses rollers that roll along the tubing which causes creep and stretching of the tubing thereby causing inaccurate amounts of medicine to be injected into the body and it creates momentary backflow pressure conditions which can have harmful effects.

SUMMARY OF THE INVENTION

The present invention relates to an infusion device and more particulaly to a portable infusion device for accurately pumping fluid medicine into a body at precise time intervals over an extended period of time so that a patient onto whom it is attached can be ambulatory.

An object of the present invention is to provide a portable infusion device that accurately pumps fluid medicine into a body.

Another object of the present invention is to provide a portable infusion device that accurately pumps fluid medicine into a body.

Another object of the present invention is the provision of a portable infusion device that includes control means for operating pump means at precise time intervals over an extended period of time.

A further object of the present invention is to provide a positive pressure pump which includes a spiral cam that is disposed within D-shaped opening of tube-engaging segments to move them at right angles with respect to the axis of the spiral cam thereby incrementally deforming the tubing along the length of the spiral cam to provide a travelling wave therealong which forces the liquid medicine positively and accurately along the tubing.

An additional object of the present invention is the provision of a pump that eliminates a backflow condition at the end of the pumping cycle.

A still further object of the present invention is to provide a programmable control means for automatically operating the pump at selected periodic intervals.

Still another object of the present invention is the provision of a portable infusion device for ambulatory out-patient use which is light weight, simple, durable dependable and entirely self-contained.

A still additional object of the present invention is to provide a portable infusion device having a reservoir that holds the fluid medicine which is latchably mounted onto the pump and control housing, the reservoir including a plunger that seals the fluid medicine therein and it operates as a moving indicator of the amount of medicine in the reservoir.

Still a further object of the present invention is the provision of a sealing plunger for a reservoir and which has an extention of reduced thickness that seals the opening through which the medicine passes when the medicine has been removed from the reservoir in order to prevent the passage of air through the opening.

Still an additional object of the present invention is to provide an alarm means as part of the electronic control circuit for a portable infusion device in order to indicate improper operation of the device.

These and other objects of the invention will appear more fully from the following description and the accompanying drawings illustrating preferred embodiments of the invention. It is to be understood that changes may be made from the exact details shown and described without departing from the principles of the invention.

BRIEF DESCRIPTION OF THE DRAWINGS

FIG. 19 is an elevational view of the left end of FIG. 18;

DETAILED DESCRIPTION OF THE INVENTION

As illustrated, the portable infusion device is designed primarily for precisely injecting accurate amounts of medicinal fluid during ambulatory intravascular therapy, but it is obvious that the device may, with or without modification, be used for various and sundry other purposes including precise feeding during extended periods of travel such as space flights, precise injections of fluid into animals and the like.

Figure 1:
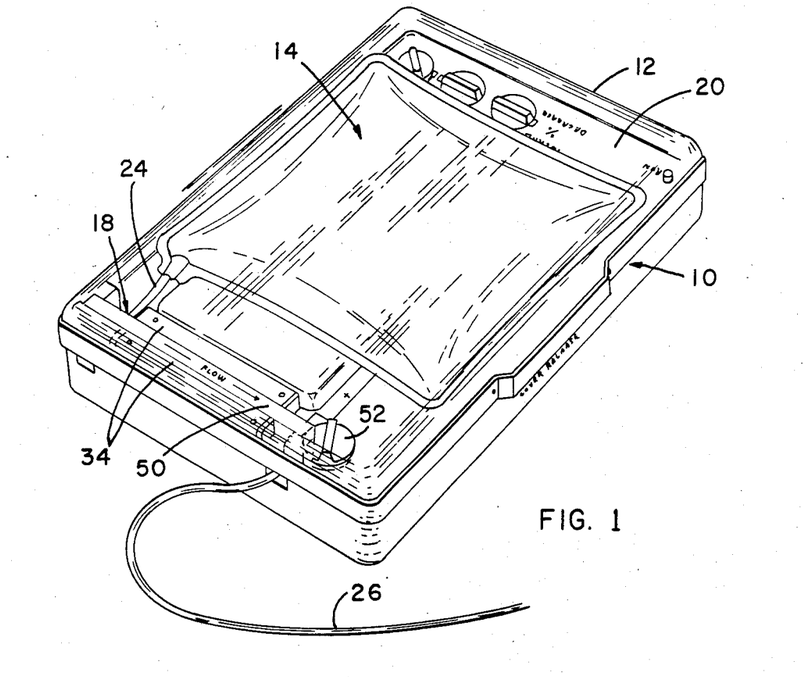
FIG. 1 is a perspective view of the portable infusion device.
Figure 2:
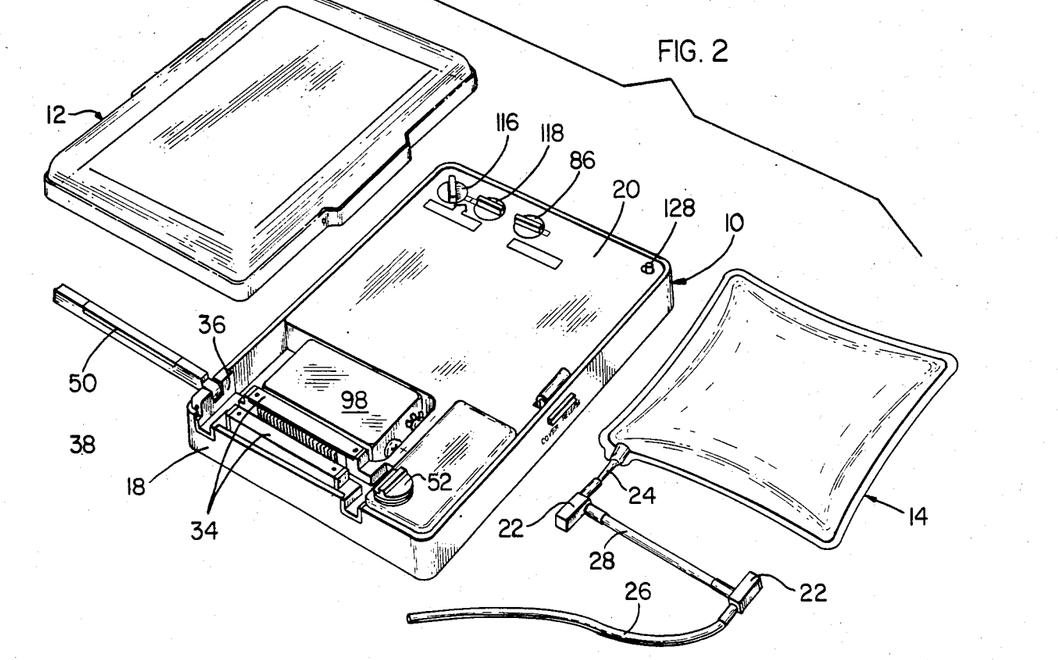
FIG. 2 is a perspective exploded view of parts of the portable infusion device.

The portable infusion device, as illustrated in FIGS. 1-5, comprises a case 10, a cover 12, infusate bag 14. Case 10 is a pan-shaped member in which a control circuit board 16 and pump 18 are disposed. A plate 20 is positioned over control circuit board 16 to protect the compoments thereon and to provide a mounting means onto which infusate bag 14 is disposed. Cover 12 is preferably molded from transparent plastic which snaps into a secured position onto case 10 to maintain infusate bag 14 in position and protect it and to readily discern amount of infusate therein. Coupling members 22 connect to tubing 24 of the infusate bag 14 and tubing 26 which is to be connected to the body via a needle (not shown). Tubing 28 is connected between coupling members 22 and is secured in pump 18. The self-contained portable infusion device as illustrated in FIG. 1 is readily applied on a patient's body via a harness (not shown) or as desired.

Figure 3:
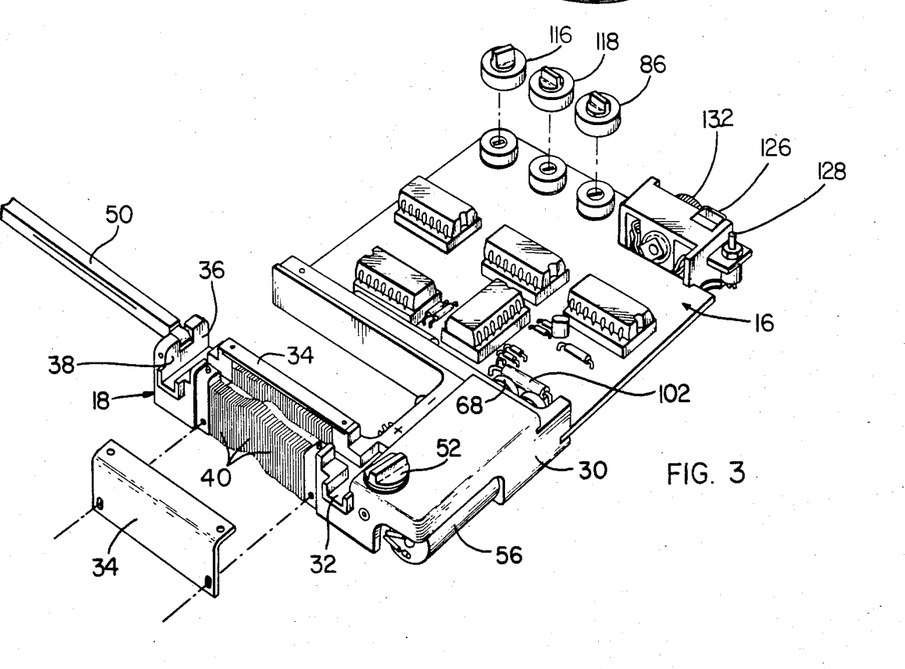
FIG. 3 is a perspective view with parts exploded therefrom of the operating part of the portable infusion device.
Figure 5:
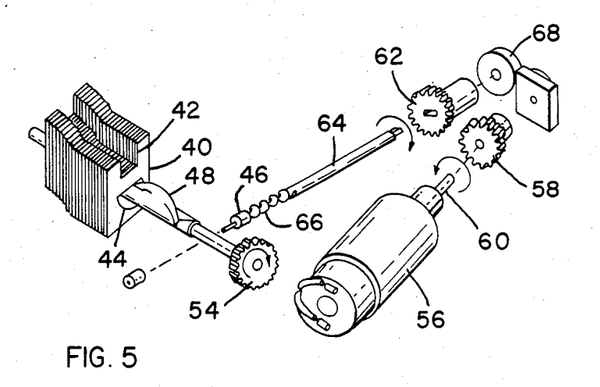
FIG. 5 is a perspective exploded view of the pump and drive therefor.

Pump 18 includes a frame 30 having a T-shaped channel 32 in which coupling member 22 is disposed. L-shaped plates 34 are connected between frame 30 and block 36. A T-shaped channel 38 is disposed in block 36 and receives therein coupling member 22. Tube-engaging segments 40 are movably mounted between frame 30 and block 36 within the area provided between L-shaped plates 34 and they are movable relative to one another. Each tube-engaging segment 40 has a U-shaped opening 42 in its upper section and a D-shaped opening 44 in its lower section. Openings 42 of segments 40 define a channel in which tubing 28 is disposed.

A rotatable drive member 46 has a spiral cam 48 thereon which wraps around drive member 46 over 360°. Spiral cam 48 is disposed through D-shaped openings 44 of segments 40 to maintain them in position and to reciprocably move them during rotation of spiral cam 48 via drive member 46. L-shaped plates 34 maintain segments 40 in position to guide them during their reciprocatory movement.

A stationary pressure plate 50 is pivotally mounted on block 36 and is secured in position against tubing 28 when it is disposed in the channel formed by U-shaped openings 42 in segments 40 by means of rotatable knob 52 which engages an end of plate 50. The legs of U-shaped openings 42 move on each side of pressure plate 50 as a result of the movement of spiral cam 48 within openings 44 and this action depresses tubing 28 against pressure plate 50 as described hereafter.

Figures 4A, 4B:
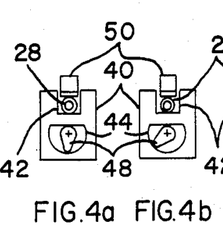
FIGS. 4a–4h illustrate the movement of one tube-engaging segment during rotational movement of the spiral cam.
Figure 4C:
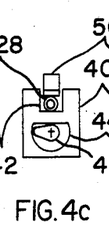
Figures 4D, 4E:
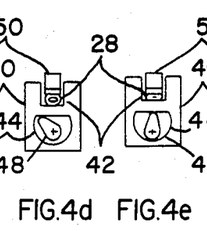
Figures 4F, 4G, 4H:
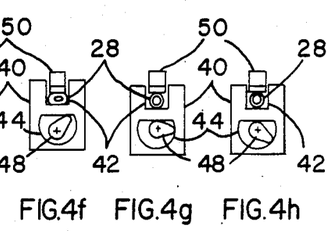

FIGS. 4a-4h illustrate the reciprocal movement of a tube-engaging segment 40 during one revolution of sprial cam 48. While sprial cam 48 is moving in the arcuate part of D-shaped opening 44 defining a cam follower means, segment 40 is stationary as shown by FIGS. 4a-4c; however, when sprial cam 48 engages and moves along the flat part of D-shaped opening 44, segment 40 moves from the rest position to an upper maximum position to the rest position again against tubing 28 and relative to pressure plate 50 as shown by 4d-4f whereby tubing 28 is moved from a fully open position to a closed position and then to a fully open position in the area of engagement by such segment. Segment 40 remains stationary during movement in the arcuate part of D-shaped opening 44 as shown in FIGS. 4g, 4h and 4a.

Thus, due to the spiral configuration of spiral cam 48 moving within cam follower openings 44 of tube-engaging segments 40, a constantly-occuring traveling wave is linearly formed along tubing 28 to positively pump the liquid medicine from infusate bag 14 into the patient's body. The linear traveling wave as formed along tubing 28 via reciprocal movement of segments 40 pinching tubing 28 against pressure plate 50 under the action of spiral cam 48 and cam follower openings 44 constitutes peristaltic action. The perpendicular motion of segments 40 with respect to tubing 28 eliminates creep and stretching of the tubing and produces positive pumping pressure.

In order to eliminate momentary backflow pressure at the end of each peristaltic cycle, it has been found that if the D-shaped cam follower opening 44 are altered and selected configurations of such altered cam follower openings are utilized along the spiral cam, backflow is indeed eliminated.

Figure 6A:
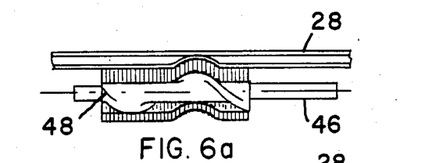
FIGS. 6a, 6b, 7a, 7b, 8a, 8b, 9a, 9b, 10a, 10b, 11a, 11b, 12a and 12b are side elevational views and end elevational views, respectively, showing travelling wave forms and the configurations of the cam-following openings in the tube-engaging segments of the pump.
Figure 6B:
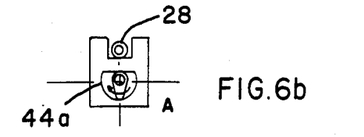
Figure 7A:
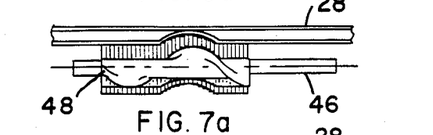
Figure 7B:
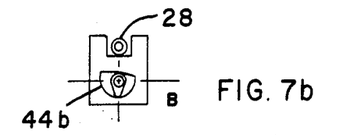
Figure 8A:
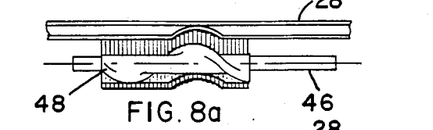
Figure 8B:
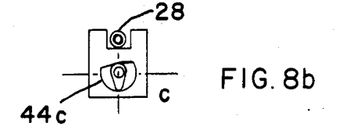
Figure 9A:
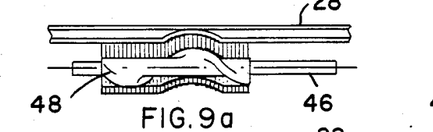
Figure 9B:
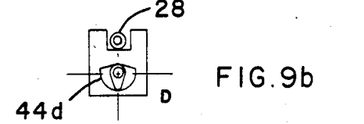
Figure 10A:
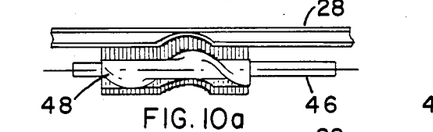
Figure 10B:
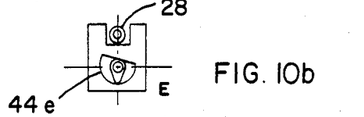
Figure 11A:
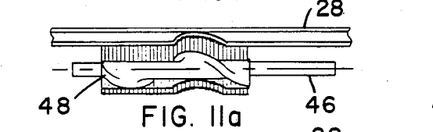
Figure 11B:
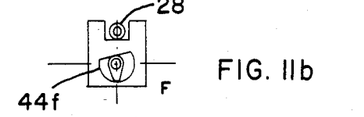
Figure 12A:
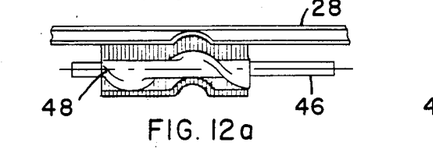
Figure 12B:
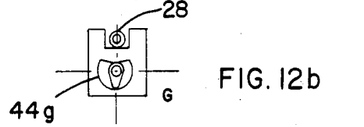

FIGS. 6a and 6b illustrate cam-follower opening 44a to be the same as cam-follower opening 44 whereby the upper part of opening 44a is flat or has a zero slope and constitutes a configuration A providing a uniform traveling wave. Cam-follower opening 44b of FIGS. 7a and 7b defining configuration B has a slightly arcuate upper part with a negative slope and this configuration provides a traveling wave having a positive slope longer than the negative slope. Cam-follower opening 44c of FIGS. 8a and 8b constituting configuration C is opposite in shape to that of cam-follower opening 44b of FIGS. 7a and 7b thus providing a traveling wave having a positive slope shorter than the negative slope. FIGS. 9a and 9b illustrate cam-follower opening 44d defining configuration D which has an upper part of uniform arcuate configuration thereby providing a traveling wave like the traveling wave of FIGS. 6a and 6b but longer. Cam-follower opening 44e of FIGS. 10a and 10b defines configuration E and its upper part has a negative slope so that the traveling wave is similar to but shorter than the traveling wave of FIGS. 7a and 7b. FIGS. 11a and 11b illustrate cam-follower opening 44f defining configuration F which is opposite in configuration to camfollower opening 44e of FIGS. 10a and 10b and provides a traveling wave similar to but shorter than that of FIGS. 8a and 8b. Cam-follower opening 44g of FIGS. 12a and 12b defining configuration G has a V-shaped upper part so that the traveling wave is similar to that of FIGS. 6a and 6b but of shorter duration.

Figure 13A:
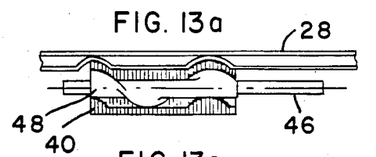
FIGS. 13a–13d are side elevational views of the operation of tube-engaging segments selected from FIGS. 6–12 to eliminate backflow conditions.
Figure 13B:
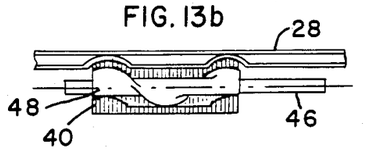
Figure 13C:
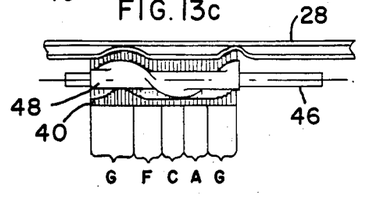
Figure 13D:
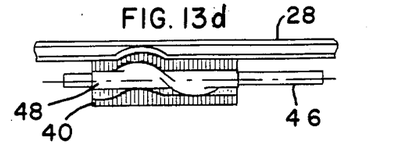

By combining cam-follower openings having configurations G,F,C,A and G in segments 40 as illustrated in FIG. 13c, the segments forming the exiting traveling wave make the wave diminish slowly whereas the segments forming the entering traveling wave make its volume increase. In this way, the loss in volume of the exiting traveling wave is exactly made up by the increase in volume of the entering traveling wave thereby providing a volume change of zero which eliminates a pressure drop and backflow condition, thus, flow rate is maintained constant. Other configurations of the cam-follower openings can of course be realized to attain the intended result.

FIG. 5 illustrates a driving mechanism for driving the spiral cam 48 and drive member 46 having a worm gear 54 secured thereto. A DC electric-motor 56 has a spur gear 58 secured on its shaft 60. Spur gear 58 meshes with another spur gear 62 which is secured onto shaft 64 having a worm 66 meshing with worm gear 54 to drive the same. A disc magnet 68 is mounted onto spur gear 62 so that when driving mechanism is in operation, disc magnet 68 pulses the electronic control system hereinafter described.

Figure 14:
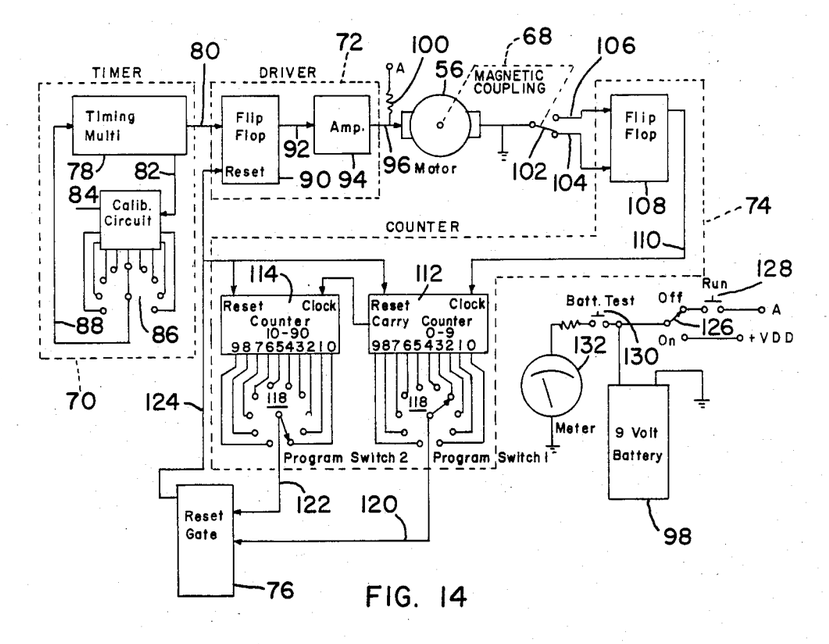
FIG. 14 is a block diagram of the electronic control means for operating the pump.

FIG. 14 is a block diagram of the electronic control circuit means for operating the drive motor 56. The circuit means is made from conventional discrete components comprising active, passive as well as digital CMOS integrated circuits which are commercially available. They are connected in such a manner on printed circuit board 16 to form a programmable counter comprising a timer circuit 70, a driver circuit 72, a counter circuit 74 and a reset gate 76.

Timer circuit 70 comprises a free running non symmetrical timing multivibrator 78 that produces a low voltage output for about 140 seconds and a high voltage output for about one second on output lead 80. Another output 82 feeds into calibration circuit 84 from timing multivibrator 78. Calibration circuit 84 defines an RC network with different values of resistors connected to the stationary contacts of a single pole multi-position switch 86 whereby the wiper contact thereof provides an output on output lead 88 connected thereto which is connected to the input of timing multivibrator 78 to provide selected RC values to timing multivibrator 78 in order to increase or decrease the time when timing multivibrator 78 produces an output trigger pulse on lead 80 which triggers a flip-flop circuit 90 to provide an output on lead 92 into amplifier 94 comprising an NPN transistor which is used as an emitter follower with motor 56 connected to the emitter via lead 96.

Operation of motor 56 operates reed switch 102 via disc magnet 68 to magnetically operate the movable contact of reed switch 102 alternately between its stationary contacts thereof which are connected to input leads 104 and 106 connected to flip-flop circuit 108. The movement between the stationary contacts of the reed switch 102 generates input pulses into flip-flop circuit 108 on input leads 104 and 106 and flip-flop circuit 108 acts as a wave shaper to shape the input pulses into smoother pulses and also to eliminate contact bounce created in the reed switch. The output from flip-flop circuit 108 on lead 110 is fed into cascade-connected decimal counters 112 and 114. Counter 112 is for units and counter 114 is for tens so that a count of ninety nine can be achieved. Other decimal counters can be connected in cascade to provide a higher count if desired.

The outputs of counters 112 and 114 are connected to the stationary contacts of single pole, multiposition switches 116 and 118. The movable contacts of switches 116 and 118 are connected to input leads 120 and 122 which are connected to a reset gage 76. Flip-flop circuit 108, counters 112, 114 and switches 116 and 118 comprise programmable counter circuit 74. The output from reset gate 76 is provided on lead 124 which is connected to flip-flop circuit 90 and counters 112 and 114 to reset these circuits to zero state to await the generation of another trigger pulse from timing multivibrator 78 whereafter the control circuit operates for the number of counts determined by the position of the movable contacts of switches 116 and 118.

As shown by the position of switches 116 and 118 in FIG. 14, the control circuit will operate after generation of a repetitive trigger pulse for three counts which means three makes and breaks of reed switch 102 whereupon reset gate 76 generates a reset pulse on lead 124 to reset flip-flop circuit 90 and counter circuits 112 and 114 to zero state. About every 140 seconds, depending on the setting of switch 86, another trigger pulse will be generated and the control circuit willrepeat its operation in accordance with the setting of switches 116 and 118. This will determine the precise amount of rotational motion by motor in operation which will pump a predetermined accurate amount of medication into a body via the operation of pump 18 over a twenty four hour period.

An on off switch 126 is provided to operate the control circuit in its automatic mode of operation or to operate it by actuation of push-button switch 128. A battery test circuit comprising push-button switch 130 and meter 132 is provided to make certain the battery 98 is operative to supply the necessary power for operation of the portable infusion device.

Figure 15:
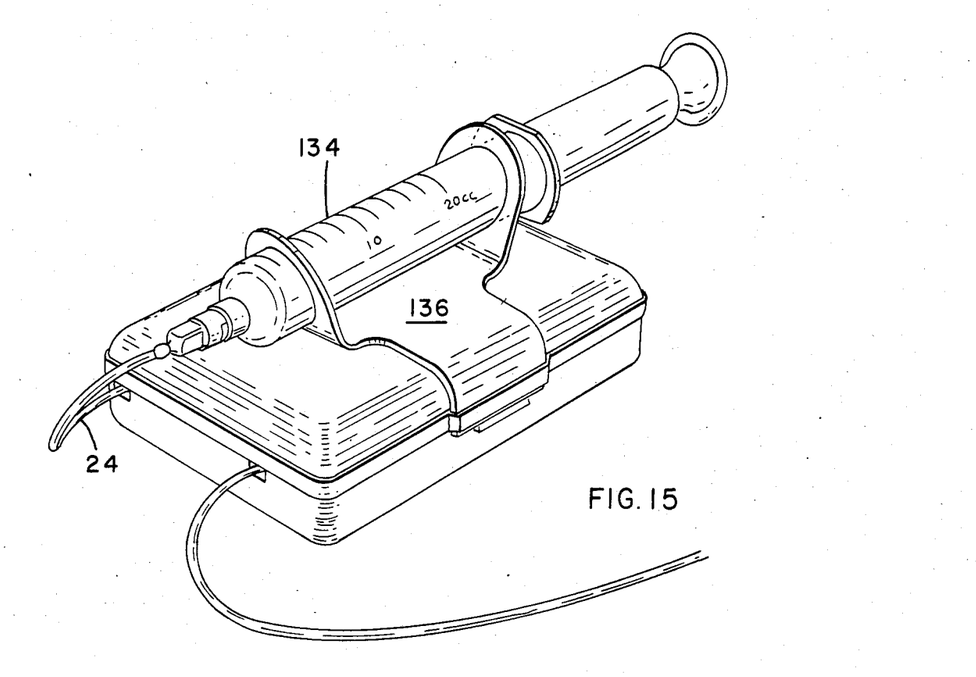
FIG. 15 is a perspective view of an alternative embodiment.

An alternative embodiment is shown in FIG. 15 wherein a hypodermic syringe 132 is clamped onto cover 12 via clamp 136 and tube 24 is connected thereto. This can provide a visual indication of the amount of medicine that has been used.

The positive terminal of battery 98 is connected to lead 96 through resistor 100 and motor 56 operates via switches 126 and 128 to provide an optimal manual run mode. Normal mode of operation occurs with switch 126 in the on position.

FIGS. 16–22 illustrate a further embodiment of the portable infusion device and it comprises a case 140, a transparent cover 142 hingeably mountable on case 140 and a reservoir 144 in which liquid medicine is contained. Case 140 is substantially the same as case 10 since it contains the electronic control circuitry and pump 18 controlled thereby. Thus, the same reference numerals where applicable will be used to identify the members common to the FIGS. 1 and 17 embodiments.

Figure 16:
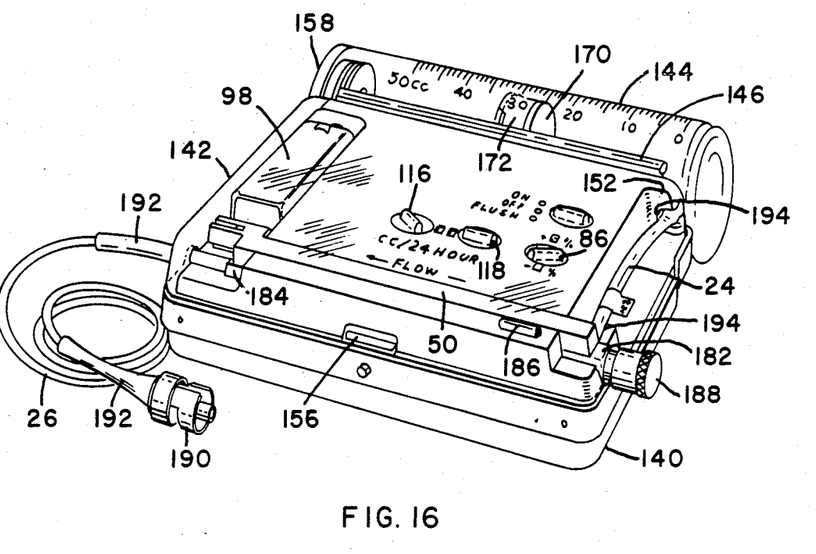
FIG. 16 is a perspective view of a further embodiment.
Figures 17, 18, 20, 21:
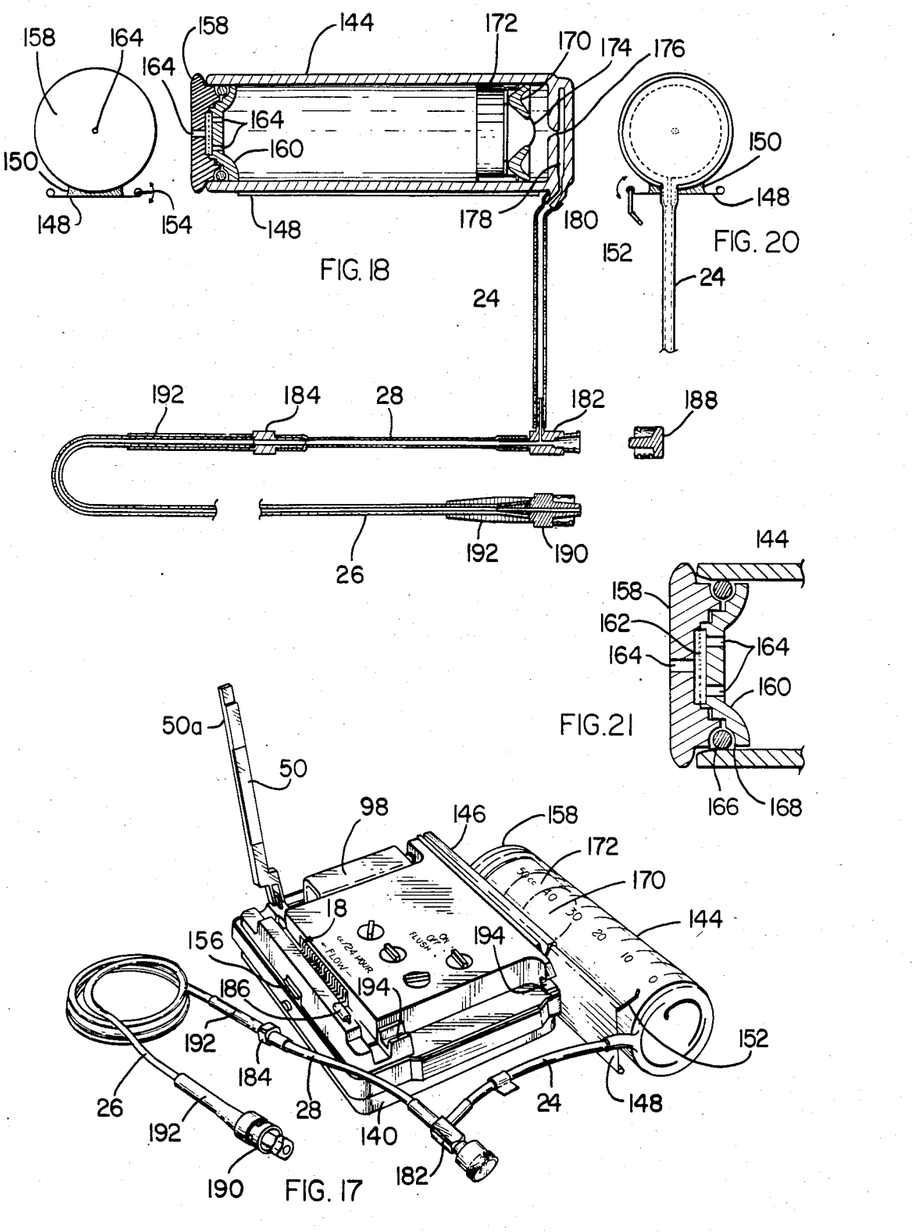
FIG. 17 is another perspective view of the embodiment of FIG. 16 with parts positioned in non-operating positions; and with no cover.
FIG. 18 is a cross-sectional view of the reservoir for the fluid medicine.
FIG. 20 is an elevational view of the right end of FIG. 18.
FIG. 21 is an enlarged cross-sectional view of the closure cap for the reservoir.

Retaining members 146 (only one being shown) are provided on the rear section of case 140 and they form a channel to receive a plate 148 secured onto reservoir 144. Plate 148 is secured to reservoir 144 by means of a silicone elastomer adhesive 150 which acts as a shock absorbing mount. Reservoir 144 is made of PYREX glass and has a measuring scale in cubic centimeters thereon.

The ends of plate 148 form a tubular channel in which a wire lock is disposed. Ends 152 and 154 of the wire lock extend at right angles to the wire from which they depend and they are positioned at right angles to each other so that end 152 rests against reservoir 144 and end 154 extends toward mount 150 when the reservoir is positioned on case 140 and removed thereon. When plate 148 has been positioned in retaining members 146, end 152, the operating end, is moved about 180° in engagement with case 140 as shown in FIG. 16, ends 152, 154 thereby locking plate 148 in position in retaining members 146. With cover 142 in position, on case 140, and latched in position thereon via latch 156, operating end 152 is prevented from moving to a position to unlock the wire lock which therefore prevents the reservoir from accidentally being separated from the case.

A cap 158 is secured onto the end of reservoir 144. A section 160 is provided in cap 158 and section 160 secures a sterilizable bacteria filter 162 in position in cap 158. Bacteria filter 162 is made of TEFLON plastic which is commercially available. Openings 164 are provided in cap 158 and section 160 to permit sterilized air within the reservoir. Due to the presence of bacteria filter 162, reservoir 144 can be refilled without resterilizing it. An O-ring 166 is disposed within annular groove 168 formed between cap 158 and section 160 to form a seal between reservoir 144 and cap 158.

An elastomer plunger 170, which is made of silicone, is mounted on a stainless steel cup 172. Plunger 170 seals the fluid medicine in reservoir 144 and is guided therealong by cup 172. Plunger 170 also defines an indicating means for indicating a continuous and accurate indication of the quantity of medicine remaining in reservoir 144.

Plunger 170 contains a thin-sectioned soft button-shaped area 174 which seals small orifice 176 at the inner end of reservoir 144 if reservoir 144 is accidently emptied. This prevents any possibility of air injection into a patient and provides a positive shut-off valve when reservoir 144 is emptied.

Chamber 178 is located at the inner end of reservoir 144 and is in communication with the reservoir via orifice 176. Chamber 178 provides an air trap and the fluid medicine exits air trap chamber 178 through an opening in nipple 180 onto which is fitted an end of tubing 24. The other end of tubing 24 is fitted onto a stainless steel adaptor 182 which also has one end of tubing 28 connected thereto. The other end of tubing 28 is fitted onto stainless steel coupling member 184. Tubing 28 is fitted into pump 18 when pressure bar 50 is moved to a non-operating position as shown in FIG. 17; then pressure bar 50 is moved to an operating position as shown in FIG. 16, a pin 50a is provided on pressure bar 50 which mates with a hole in spring locking member 186 which locks the pressure bar 50 in operating position.

Cover 142 maintains locking member 186 in position so that the locking member does not permit pin 50a from accidently becoming unlocked. Adaptor 186 will accept any standard syringe for refilling reservoir 144 and it is capped by cap 188 when the device is in normal operation. Tubing 26 is fitted onto coupling member 184 and onto a stainless steel coupling member 190 which connects with another coupling member leaving a tubing and needle thereon (not shown). The tubing connections on the nipple 180, adaptor 182 and coupling members 184 and 190 are bonded by a silicone elastomer adhesive and silicone rubber boots 192 are provided on tubing 26 where it connects to coupling members 184 and 190 to protect such connections because of movement at these connections. U-shaped members 194 are provided on case 140 to receive nipple 180 and adaptor 182 along with the tubing 24 thereover.

Figure 22:
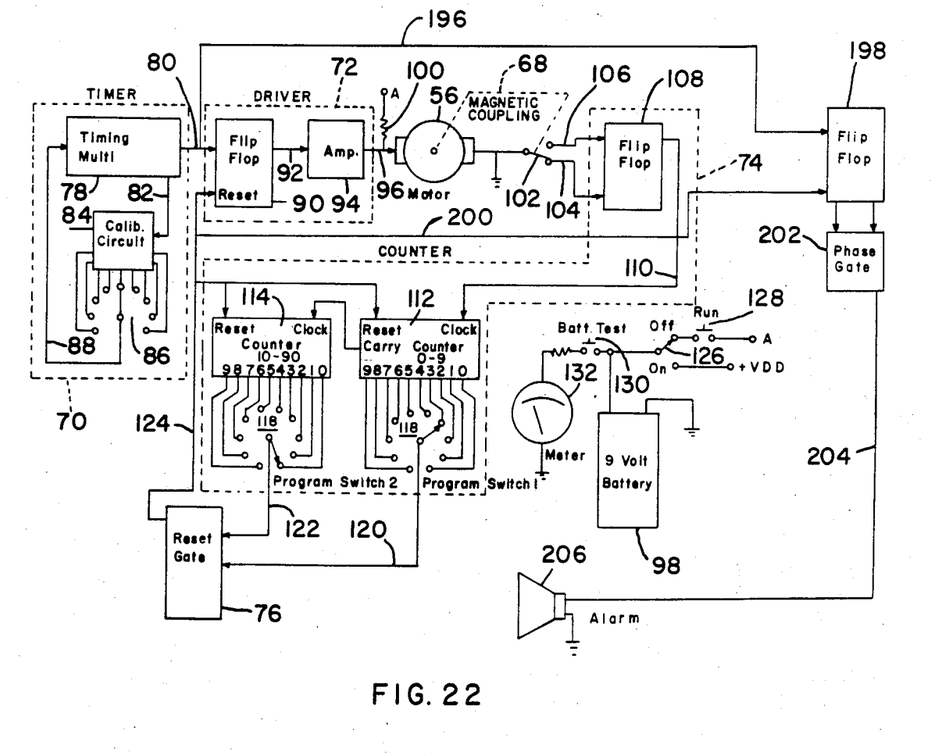
FIG. 22 is a block diagram of the improved electronic control means for operating the pump.

The operation of the portable infusion device of FIGS. 6–21 is the same as the embodiment of FIGS. 1–13, and the electronic control circuit of FIG. 22 is the same and operates in the same manner as that of FIG. 14. The control circuit of FIG. 22 includes an electronic alarm circuit to indicate a weakening battery condition, a system failure when continuous pumping action occurs, or when lack of pumping action takes place, a zero output selection and a correct and properly functioning system when the circuit is initially turned on.

The electronic alarm circuit includes lead 196 connected to output lead 80 of timing multivibrator 78 and to one input of flip-flop circuit 198. Lead 200 is connected to lead 124 and to the other input of flip-flop circuit 198. Flip flop circuit is therefore a pair of flip flops connected to receive timing pulses from timer circuit 70 and reset pulses from reset gate 76. The flip flops of flip flop circuit 198 change state with the timing pulse and with the reset pulse and as long as the control circuit produces timing pulses and reset pulses in alternating sequence, the flip flops stay in phase thereby supplying outputs to phase gate 202 that are normally in phase which will not gate 202 to send an alarm signal along lead 204 to audiple alarm 206. If for any reason as set forth above, a reset pulse is not received by flip flop circuit 198 before the next timing pulse is received by flip flop circuit 198, the outputs to gate 202 are out of phase and this causes gate 202 to generate an alarm signal that is sent via lead 204 to actuate alarm 206.

Figure 23:
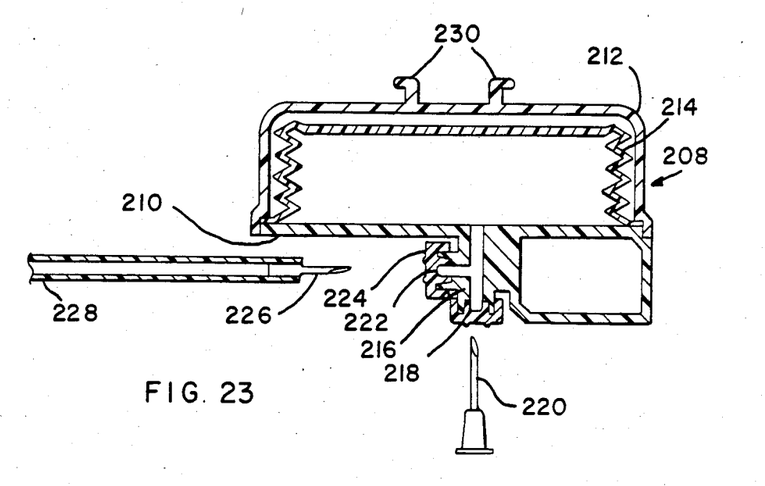
FIG. 23 is a cross-sectional view of a still further embodiment of the present invention.

FIG. 23 illustrates a still further embodiment of the present invention, and it comprises a plastic housing 208 which includes a base 210 and cap 212 that snap fits onto base 210. A plastic bellows 214 having very thin walls is secured to base 210 preferably via ultrasonic techniques.

A passageway 216 is provided in base 210 and it is covered by an elastomeric sealing member 218. Passageway 216 communicates with the interior of bellows 214 and a needle 220 from a syringe (not shown) is inserted through sealing member 218 to fill bellows 214 with a desired liquid medicine. Bellows 214 acts as a reservoir for such medicine. Cap 212 protects bellows 214 and it can be transparent plastic material. When needle 220 is removed, sealing member 218 seals itself.

Another passageway 222 communicates with passageway 216 and it is covered by elastomeric sealing member 224. Needle 226 having tubing 228 secured thereto is inserted through sealing member 224. Projections 230 are provided by cap 212 which mate with retaining members 146 of case 140 of FIG. 17 to mount housing 208 thereon. Tubing 228 is then placed within pump 18 and the portable infusion device operates in the same manner as that of FIGS. 1–13 and 16–21 under the control circuit of FIG. 22.

Although the invention has been explained with reference to the particular embodiments, it is to be appreciated that various adaptations and modifications may be made without departing from the appended claims.

The invention is claimed in accordance with the following:

1. An infusion device for infusing a fluid medicine into a body and to be carried thereby comprising;
   a case having mounting means thereon;
   reservoir means disposed in said mounting means for carrying the fluid medicine, said reservoir means having cap means closing one end thereof and said cap means having bacteria filter means provided therein, tubing means connected to said reservoir means;

pump means provided by said case and having a portion of said tubing means disposed therein; motor means for operating said pump means; and control circuit means connected to motor means for operating said motor means including signal generating means that generate signals according to the rotations of said motor means, programmable means for receiving said signals and for stopping operation of said motor means after a selected number of rotations of said motor means, means for selecting the selected number of rotations of said motor means, and means for automatically operating said motor means at selected times.

2. An infusion device according to claim 1 wherein said tubing means includes an adapter means for receiving syringe means to refill said reservoir means.

3. An infusion device according to claim 1 wherein locking means are provided for locking said reservoir means in said mounting means.

4. An infusion device according to claim 1 wherein said reservoir means has plunger means movable therealong including an elastomer sealing means sealingly engaging an inside surface of said reservoir means.

5. An infusion device according to claim 4 wherein said reservoir means includes a chamber at an inner end which is provided with an orifice enabling said reservoir and said chamber to be in communication; said elastomer sealing means having a thin-walled extension for engagement with said orfice when said plunger means reaches said chamber thereby sealing said chamber from said reservoir means.

* * * * *